United States Patent
Lee et al.

(10) Patent No.: US 11,090,324 B2
(45) Date of Patent: Aug. 17, 2021

(54) COMPOSITION, FOR REMEDYING FEMALE CLIMACTERIC SYNDROME SYMPTOMS, COMPRISING TECTORIGENIN 7-O-XYLOSYLGLUCOSIDE

(71) Applicant: LG Household & Health Care Ltd., Seoul (KR)

(72) Inventors: Bo-Young Lee, Daejeon (KR); Ho-Song Cho, Daejeon (KR); Soon-Ran Song, Daejeon (KR); Won-Kyung Lee, Daejeon (KR); Chang-Il Choi, Daejeon (KR); Sang-Hwa Lee, Daejeon (KR)

(73) Assignee: LG Household & Health Care Ltd.

( * ) Notice: Subject to any disclaimer, the term of this patent is extended or adjusted under 35 U.S.C. 154(b) by 0 days.

(21) Appl. No.: 16/491,780

(22) PCT Filed: Jul. 18, 2017

(86) PCT No.: PCT/KR2017/007716
§ 371 (c)(1),
(2) Date: Sep. 6, 2019

(87) PCT Pub. No.: WO2018/164324
PCT Pub. Date: Sep. 13, 2018

(65) Prior Publication Data
US 2020/0030350 A1     Jan. 30, 2020

(30) Foreign Application Priority Data
Mar. 7, 2017  (KR) .......................... 10-2017-0028999

(51) Int. Cl.
*A61K 31/7048*     (2006.01)
*A23L 33/10*      (2016.01)

(52) U.S. Cl.
CPC .......... *A61K 31/7048* (2013.01); *A23L 33/10* (2016.08)

(58) Field of Classification Search
None
See application file for complete search history.

(56) References Cited

U.S. PATENT DOCUMENTS

2014/0234271 A1   8/2014  Miller et al.

FOREIGN PATENT DOCUMENTS

WO   2005105125 A1   11/2005

OTHER PUBLICATIONS

Park, Phytochemistry 51 (1999) 147-151. (Year: 1999).*
Kamiya, Biosci. Biotechnol. Biochem. 76(8), 1511-1517, 2012. (Year: 2012).*
International Search Report for Application No. PCT/KR2017/007716 dated Dec. 4, 2017.
Kamiya, T. et al., Evaluation of the Estrogenic Activity of Pueraria (Kudzu) Flower Extract and Its Major Isoflavones Using ER-binding and Uterotrophic Bioassays, Pharmacology & Pharmacy, 2013, vol. 4, pp. 255-260.
Yamazaki, T. et al., The Protective Effect of a Puerariae Flos Extract (thomsonide) against Ethanol-induced Gastric Lesions in Rats, Pharmacology & Pharmacy, 2016, vol. 7, pp. 208-215.
Tanaka, T. et al., Kudzu (Pueraria lobata) Vine Ethanol Extracts Improve Ovariectomy-induced Bone Loss in Female Mice, Journal of Agriculture and Food Chemistry, Nov. 2011, vol. 59, pp. 13230-13237.
Lu, J. et al., Simultaneous Determination of Isoflavones, Saponins and Flavones in Flos Puerariae by Ultra Performance Liquid Chromatography Coupled with Quadrupole Time-of-flight Mass Spectrometry, Chemical and Pharmaceutical Bulletin, Jun. 2013, vol. 61, No. 9, pp. 941-951.
Hyun-Jung Park et al., "The Effects of Puerariae Flos on Stress-induced Deficits of Learning and Memory in Ovariectomized Female Rats," Korean J Physiol Pharmacol, vol. 13, p. 85-89, Apr. 2009, No. 2.
Yujiro Niiho et al., "Simultaneous analysis of isoflavones and saponins in Pueraria flowers using HPLC coupled to an evaporative light scattering detector and isolation of a new isoflavone diglucoside," J Nat Med, 2010, p. 313-320, vol. 64, No. 3.
Wichai Cherdshewasart et al., "Evaluation of the Estrogenic Activity of the Wild Pueraria mirifica by Vaginal Cornification Assay," Journal of Reproduction and Development, 2007, vol. 53, No. 2, p. 385-393.
Yasuyoshi et al., "Superiority of aglycon isoflavone in equol metabolic capacity inside the body," Journal of Clinical and Experimental Medicine, Jun. 27, 2015, vol. 253, No. 13, p. 1263-1264.

* cited by examiner

*Primary Examiner* — Layla D Berry
(74) *Attorney, Agent, or Firm* — Lerner, David, Littenberg, Krumholz & Mentlik, LLP

(57) ABSTRACT

The present disclosure relates to a composition for preventing, treating or remedying female climacteric syndrome symptoms, which contains tectorigenin 7-O-xylosylglucoside. The composition according to the present disclosure shows quick effects for preventing, remedying and/or treating female climacteric syndrome symptoms, particularly facial flushing and/or osteoporosis, and thus can be utilized for the hormone replacement therapy (HRT) used for preventing or remedying climacteric syndrome symptoms.

17 Claims, 2 Drawing Sheets

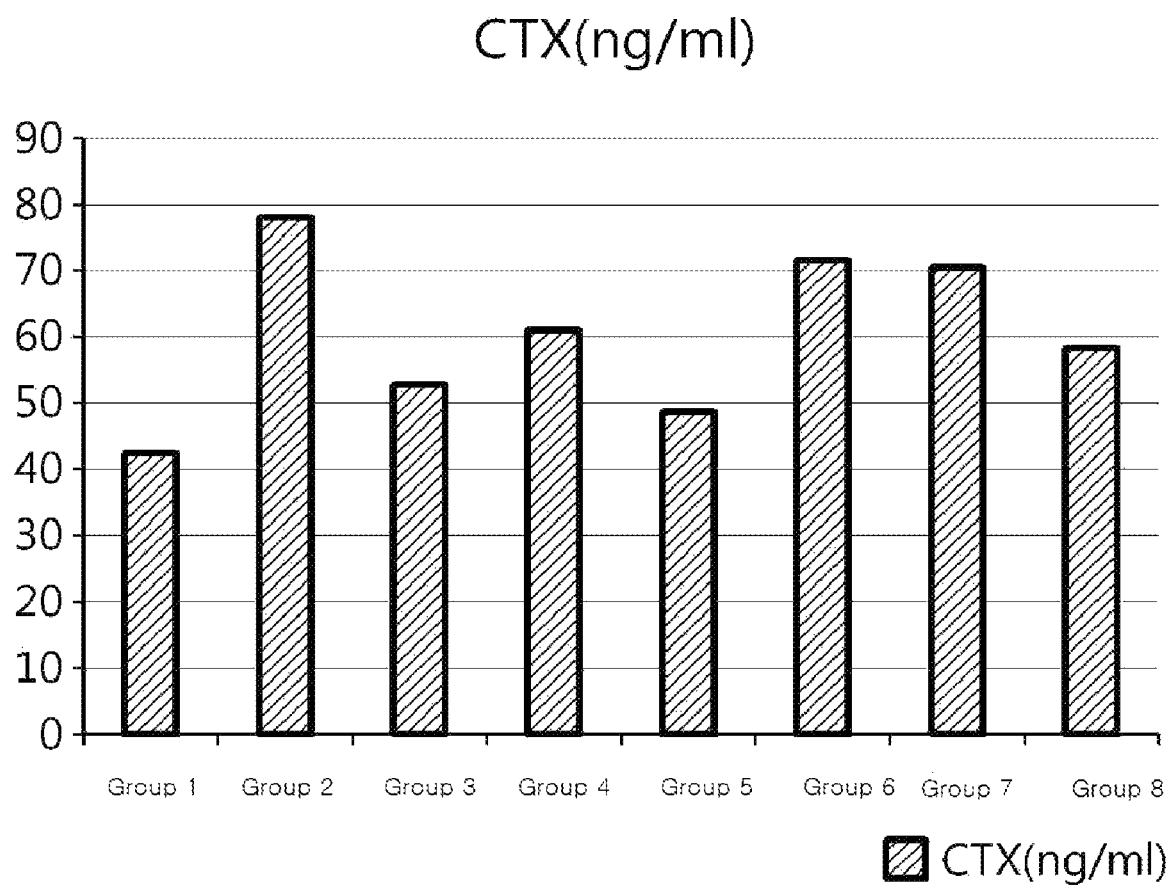

COMPOSITION, FOR REMEDYING FEMALE CLIMACTERIC SYNDROME SYMPTOMS, COMPRISING TECTORIGENIN 7-O-XYLOSYLGLUCOSIDE

CROSS-REFERENCE TO RELATED APPLICATIONS

The present application is a national phase entry under 35 U.S.C. § 371 of International Application No. PCT/KR2017/007716 filed Jul. 18, 2017, which claims priority from Korean Patent Application No. 10-2017-0028999 filed Mar. 7, 2017, all of which are incorporated herein by reference.

TECHNICAL FIELD

The present disclosure relates to a composition for preventing, remedying and/or treating female climacteric syndrome symptoms, more particularly to a composition which is particularly effective in preventing, remedying and/or treating facial flushing and/or osteoporosis among the female climacteric syndrome symptoms. The present disclosure also relates to a method for preventing, remedying and/or treating climacteric syndrome symptoms, more particularly to a method for preventing, remedying and/or treating facial flushing, and/or osteoporosis among the female climacteric syndrome symptoms.

BACKGROUND ART

Women's climacteric (menopause) refers to the stopping of menstruation occurring around 50 years of age as the ovaries stop functioning. It means the loss of reproductive capability and is a physiological change rather than a pathological phenomenon. At present, the average life span of Korean women is 81.2 years (National Statistical Office, 2011). Suppose that the average age when the menopause occurs in Korean women is 50 years as reported by the Korean Society for Obstetrics and Gynecology, they live more than about ⅓ of their lives with depleted female hormone (Sung-Chul Kim, Korea Pharmaceutical Information Center).

With the menopause, women experience changes throughout the body including the blood vascular system, musculoskeletal system, genitourinary system, cranial nerves, etc. due to the imbalance and decrease of female hormone secretion. That is to say, they experience vasomotor symptoms and psychological symptoms such as facial flushing, night sweating, sleep disorder, fatigue, depression, anxiety, attention deficit and memory impairment, sexual pain due to the contraction of the genitourinary system, oliguria, loss of skin elasticity due to decreased collagen, skin elasticity, and various diseases such as dementia, etc. (non-patent document 1). Although there are differences among individuals, it is reported that the quality of life of women worsen as they experience more and severer climacteric syndrome symptoms (non-patent document 2). In addition, it is highly likely that the climacteric syndrome symptoms will develop into chronic diseases with physical aging.

Hormone therapy, drug therapy, exercise therapy or diet may be used for treatment of the climacteric syndrome symptoms. However, the most frequently used female hormone therapy can increase the risk of breast cancer, etc. and a long-term use can increase the occurrence of uterine cancer, thrombotic vascular diseases, gallbladder diseases and hypertension. Therefore, a lot of researches are being carried out recently on phytoestrogens which are reported to have similar functions as estrogen in order to replace the estrogen therapy and other drug therapies (non-patent document 3).

It is reported that 89% of women who have experienced natural menopause experience at least one of menopausal symptoms and climacteric syndrome symptoms are also common. The inventors of the present disclosure have developed a substance capable of improving climacteric syndrome symptoms and effectively improving climacteric facial flushing and osteoporosis, and have completed a composition for preventing or remedying female climacteric syndrome symptoms, which contains tectorigenin 7-O-xylosylglucoside.

DISCLOSURE

Technical Problem

The present disclosure is designed to solve the problems of the related art and is directed to providing a composition for treating, preventing or remedying sweating, facial flushing and/or osteoporosis from among female climacteric syndrome symptoms.

The present disclosure is also directed to providing a method for treating, preventing or remedying sweating, facial flushing and/or osteoporosis from among female climacteric syndrome symptoms.

The present disclosure is also directed to providing a composition capable of maintaining the effect of treating or remedying female climacteric syndrome symptoms.

Technical Solution

An exemplary embodiment of the present disclosure provides a use of tectorigenin, tectoridin, tectorigenin 7-O-xylosylglucoside or a mixture thereof for preparation of a composition for treating, preventing or remedying female climacteric syndrome symptoms, sweating, facial flushing and/or osteoporosis.

Specifically, the composition may be contained in a functional food composition or a pharmaceutical composition.

The present disclosure provides a method for treating or remedying female climacteric syndrome symptoms, sweating, facial flushing and/or osteoporosis by administering tectorigenin, tectoridin, tectorigenin 7-O-xylosylglucoside or a mixture thereof to a patient in need of treatment of the symptoms. The present disclosure also provides a method for preventing female climacteric syndrome symptoms, sweating, facial flushing and/or osteoporosis by administering tectorigenin, tectoridin, tectorigenin 7-O-xylosylglucoside or a mixture thereof to a subject in need of the symptoms.

The present disclosure provides a composition for preventing, treating or remedying female climacteric syndrome symptoms, which contains tectorigenin 7-O-xylosylglucoside.

The composition of the present disclosure may further contain tectorigenin, tectoridin, or a mixture thereof.

The use of tectorigenin 7-O-xylosylglucoside for preventing, treating or remedying climacteric syndrome symptoms is not known yet.

In particular, the use of tectorigenin 7-O-xylosylglucoside for preventing, treating or remedying facial flushing is not known yet.

An exemplary embodiment of the present disclosure provides a composition for preventing, treating or remedying facial flushing, which contains tectorigenin 7-O-xylosylglucoside.

The composition may further contain tectorigenin and tectoridin.

Another exemplary embodiment of the present disclosure provides a composition for treating, preventing or remedying osteoporosis, which contains tectorigenin 7-O-xylosylglucoside.

The composition may further contain tectorigenin and tectoridin.

Another exemplary embodiment of the present disclosure provides a composition for treating, preventing or remedying sweating, which contains tectorigenin 7-O-xylosylglucoside.

The composition may further contain tectorigenin and tectoridin.

The inventors of the present disclosure have identified that efficacy and in-vivo retention time can be improved when tectorigenin, tectoridin and tectorigenin 7-O-xylosylglucoside are used together, and have completed the present disclosure.

The tectorigenin 7-O-xylosylglucoside of the present disclosure has a chemical formula of $C_{27}H_{30}O_{15}$ and a molecular weight of 594.52. It can be represented by Chemical Formula 1.

[Chemical Formula 1]

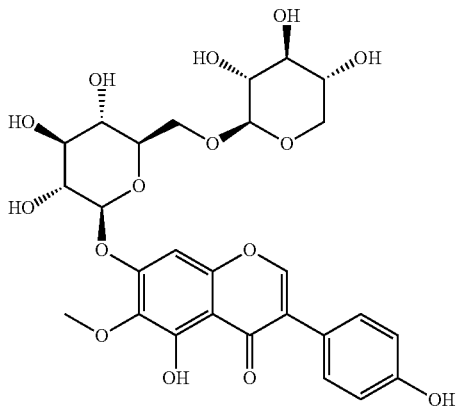

The tectorigenin of the present disclosure has a chemical formula of $C_{16}H_{12}O_6$ and a molecular weight of 300.26. It can be represented by Chemical Formula 2.

[Chemical Formula 2]

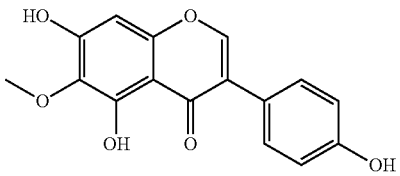

The tectoridin of the present disclosure has a chemical formula of $C_{22}H_{22}O_{11}$ and a molecular weight of 462.40. It can be represented by Chemical Formula 3.

[Chemical Formula 3]

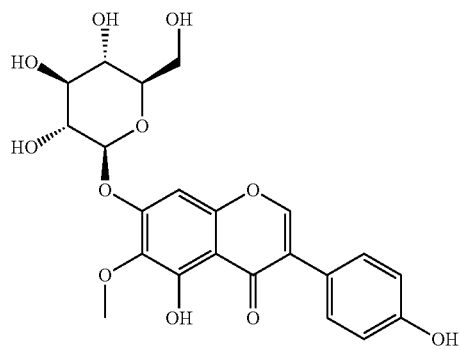

The three compounds tectorigenin 7-O-xylosylglucoside, tectorigenin and tectoridin of the present disclosure may be synthesized according to methods known in the art or may be purchased commercially.

In the present disclosure, the 'climacteric syndrome symptoms' is also called 'climacteric syndromes' or 'postmenopausal symptoms'.

In particular, the composition of the present disclosure may have an excellent effect of preventing, treating and/or remedying sweating, facial flushing or osteoporosis from among climacteric syndrome symptoms. Specifically, the composition of the present disclosure may have an excellent effect of preventing, remedying and/or treating sweating, facial flushing and osteoporosis. More specifically, the composition of the present disclosure may have an excellent effect of preventing, remedying and/or treating sweating and facial flushing.

In the present disclosure, the 'facial flushing' is the representative vasomotor symptom known to be experienced by 75% of postmenopausal women and refers to abrupt reddening of the face, neck and chest accompanied by unpleasant flushing and sweating. The climacteric vasomotor symptom occurs as the thermoneutral zone in the hypothalamus becomes narrow due to the climacteric change of hormones and hot flush is felt if the body temperature is increased only slightly.

In the present disclosure, the 'sweating' refers to secretion of sweat from the sweat glands of the skin. It is the symptom of abrupt perspiration accompanied by generation of heat.

In the present disclosure, the 'osteoporosis' refers to the state of increased risk of bone fracture due to decreased bone strength. It is caused by genetic factors, early menopause, medication, smoking, etc. Accordingly, 'climacteric osteoporosis' may be caused in women by decreased hormone production due to menopause, etc. The climacteric osteoporosis refers to the osteoporotic symptom occurring in postmenstrual women due to the imbalance of osteoblasts involved in bone formation and osteoclasts involved in bone tissue breakdown and resorption because of decreased hormone production.

In the present disclosure, 'prevention' refers to any action of inhibiting or delaying a symptom by administering the composition of the present disclosure.

In the present disclosure, 'treatment' refers to any action of improving or remedying a symptom by administering the composition of the present disclosure.

In the present disclosure, 'remedying' refers to any action of improving or favorably changing a symptom as compared to before administration by administering the composition of the present disclosure.

The compound or mixture contained in the composition of the present disclosure may be contained in an effective amount. The term 'effective amount' refers to the amount of the extract capable of inhibiting or delaying climacteric syndrome symptoms, particularly sweating, facial flushing or osteoporosis, or capable of improving the existing symptoms.

The content of the mixture contained in the composition is not particularly limited and may vary as long as sweating, facial flushing or osteoporosis can be prevented, remedied or treated. Specifically, the three compounds tectorigenin 7-O-xylosylglucoside, tectorigenin and tectoridin may be contained in the composition in an amount of 10-500 mg for a daily administration dose for climacteric women. For example, when the composition is prepared into a formulation for once-daily administration, the composition contained in the formulation may contain 10-500 mg of tectorigenin 7-O-xylosylglucoside, tectorigenin and tectoridin.

The composition may contain tectorigenin, tectoridin and tectorigenin 7-O-xylosylglucoside at a weight ratio of 1:0.5-20:0.5-20, specifically at a weight ratio of 1:0.8-15:0.8-15, more specifically at a weight ratio of 1:1.5-10:1.5-10.

If the content of each active ingredient is below the lower limit, the effect of preventing, treating or remedying sweating, facial flushing or osteoporosis may not be achieved. And, if it exceeds the upper limit, safety issue may occur.

The present disclosure may provide a cosmetic composition, a pharmaceutical composition or a food composition, which contains tectorigenin 7-O-xylosylglucoside.

In another exemplary embodiment, the present disclosure may provide a cosmetic composition, a pharmaceutical composition or a food composition, which contains a mixture of tectorigenin, tectoridin and tectorigenin 7-O-xylosylglucoside.

The composition may be provided in the form of cosmetics, medicine, food or quasi-drugs.

The pharmaceutical composition according to the present disclosure may contain a pharmaceutically effective amount of a tectorigenin 7-O-xylosylglucoside or a mixture of tectorigenin, tectoridin and tectorigenin 7-O-xylosylglucoside alone or may further contain one or more pharmaceutically acceptable carrier, excipient or diluent. The term "pharmaceutically acceptable" means that the composition is a nontoxic composition which is physiologically acceptable and usually does not cause gastroenteric trouble, allergic reactions such as dizziness or other similar reactions when administered to human, without inhibiting the action of the active ingredient.

Examples of the carrier, excipient or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, mineral oil, etc. Also, the pharmaceutical composition may further contain a filler, an anti-agglomerant, a lubricant, a wetting agent, a flavor, an emulsifier, an antiseptic, etc.

The "pharmaceutically effective amount" means an amount exhibiting a better reaction as compared to a negative control group, specifically an amount effective for exhibiting an effect of preventing, remedying and/or treating climacteric disorder.

Also, the pharmaceutical composition of the present disclosure may be formulated using a method known in the art so as to provide quick, sustained or delayed release of the active ingredient after administration to a mammal. The formulation may be in the form of a powder, a granule, a tablet, an emulsion, a syrup, an aerosol, a soft or hard gelatin capsule, a sterile solution for injection, or a sterile powder.

The pharmaceutical composition of the present disclosure may be administered orally or parenterally although the administration route is not limited thereto. The parenteral administration route includes, for example, transdermal, intranasal, intraperitoneal, intramuscular, subcutaneous or intravenous routes.

Also, the pharmaceutical composition of the present disclosure may be administered in combination with a compound known to have an effect of preventing, remedying and/or treating climacteric disorder.

In another aspect, the present disclosure provides a food composition containing one of the compositions described above.

The food composition of the present disclosure includes all types of processed forms such as food, functional food, nutritional supplement, health food, food additive, etc. The food composition may be prepared into various forms according to a common method known in the art.

For example, the health food may be taken in after being prepared into a tea, a juice, a drink, a granule, a capsule or a powder. In addition, the food composition of the present disclosure may further contain another active ingredient and/or additive that can be commonly contained in a food composition in the art.

For example, the food composition according to the present disclosure may contain a water-soluble vitamin such as thiamine (vitamin $B_1$), riboflavin, ascorbic acid, niacin and vitamin $B_6$, a fatty acid such as myristic acid, palmitic acid, stearic acid, oleic acid, linoleic acid, etc., a weak acid such as glycolic acid and acetic acid, and amino acids including 8 essential amino acids, threonine, valine, methionine, isoleucine, leucine, phenylalanine, tryptophan and lysine, aspartic acid, serine, glutamic acid, proline, glycine, alanine, cysteine, tyrosine, histidine, arginine, etc.

In another aspect, the present disclosure provides a cosmetic composition containing one of the compositions described above.

The cosmetic composition of the present disclosure may contain, in addition to the active ingredient of the present disclosure, ingredients commonly used in a cosmetic composition, for example, a common adjuvant such as an antioxidant, a stabilizer, a solubilizer, a vitamin, a pigment and a flavor, and a carrier.

The cosmetic composition according to the present disclosure may be prepared into any formulation commonly used in the art. For example, it may be formulated into a solution, a suspension, an emulsion, a paste, a gel, a cream, a lotion, a powder, a soap, a surfactant-containing cleanser, an oil, a powder foundation, an emulsion foundation, a wax foundation, a spray, etc., although not being limited thereto.

More specifically, it may be formulated into a softening lotion, a nourishing lotion, a nourishing cream, a massage cream, an essence, an eye cream, a cleansing cream, a cleansing foam, a cleansing water, a pack, a spray or a powder.

When the formulation of the present disclosure is a solution or an emulsion, a solvent, a solubilizer or an emulsifier may be used as a carrier. For example, water, ethanol, isopropanol, ethyl carbonate, ethyl acetate, benzyl alcohol, benzyl benzoate, propylene glycol, 1,3-butylene glycol, glycerol aliphatic ester, polyethylene glycol or sorbitan fatty acid ester may be used.

When the formulation of the present disclosure is a suspension, a liquid diluent such as water, ethanol or propylene glycol, a suspending agent such as ethoxylated isostearyl alcohol, polyoxyethylene sorbitol ester or polyoxyethylene sorbitan ester, microcrystalline cellulose, aluminum metahydroxide, bentonite, agar, tragacanth, etc. may be used as a carrier.

When the formulation of the present disclosure is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkyl amidobetaine, aliphatic alcohol, fatty acid glyceride, fatty acid diethanolamide, vegetable oil, lanolin derivatives, ethoxylated glycerol fatty acid ester, etc. may be used as a carrier.

When the formulation of the present disclosure is a powder or a spray, lactose, talc, silica, aluminum hydroxide, calcium silicate or polyamide powder may be used as a carrier.

In particular, when it is a spray, a propellant such as chlorofluorohydrocarbon, propane/butane or dimethyl ether may be further contained.

When the formulation of the present disclosure is a paste, a cream or a gel, animal oil, plant oil, wax, paraffin, starch, tragacanth, cellulose derivatives, polyethylene glycol, silicone, bentonite, silica, talc, zinc oxide, etc. may be used as a carrier.

Advantageous Effects

Because a composition according to the present disclosure shows quick effects for preventing, remedying and/or treating sweating, facial flushing and/or osteoporosis, it can be utilized for the hormone replacement therapy (HRT) used for preventing or remedying climacteric syndrome symptoms.

In addition, because the composition according to the present disclosure has no cytotoxicity unlike existing therapeutic agents for sweating, facial flushing or osteoporosis, and is safe with few side effects as much as it can be used as food, it can be utilized as a therapeutic agent for sweating, facial flushing or osteoporosis occurring in climacteric women.

The composition of the present disclosure, which contains a mixture of the three compounds tectorigenin 7-O-xylosylglucoside, tectorigenin and tectoridin, may provide a continued effect due to increased in-vivo retention time. Accordingly, it is effective in improving facial flushing and sweating and decreasing bone resorption.

DESCRIPTION OF DRAWINGS

FIG. 2 is a graph showing the effect of remedying bone resorption of a mixture of three compounds tectorigenin 7-O-xylosylglucoside, tectorigenin, tectoridin according to an exemplary embodiment of the present disclosure.

BEST MODE

Figure 1:
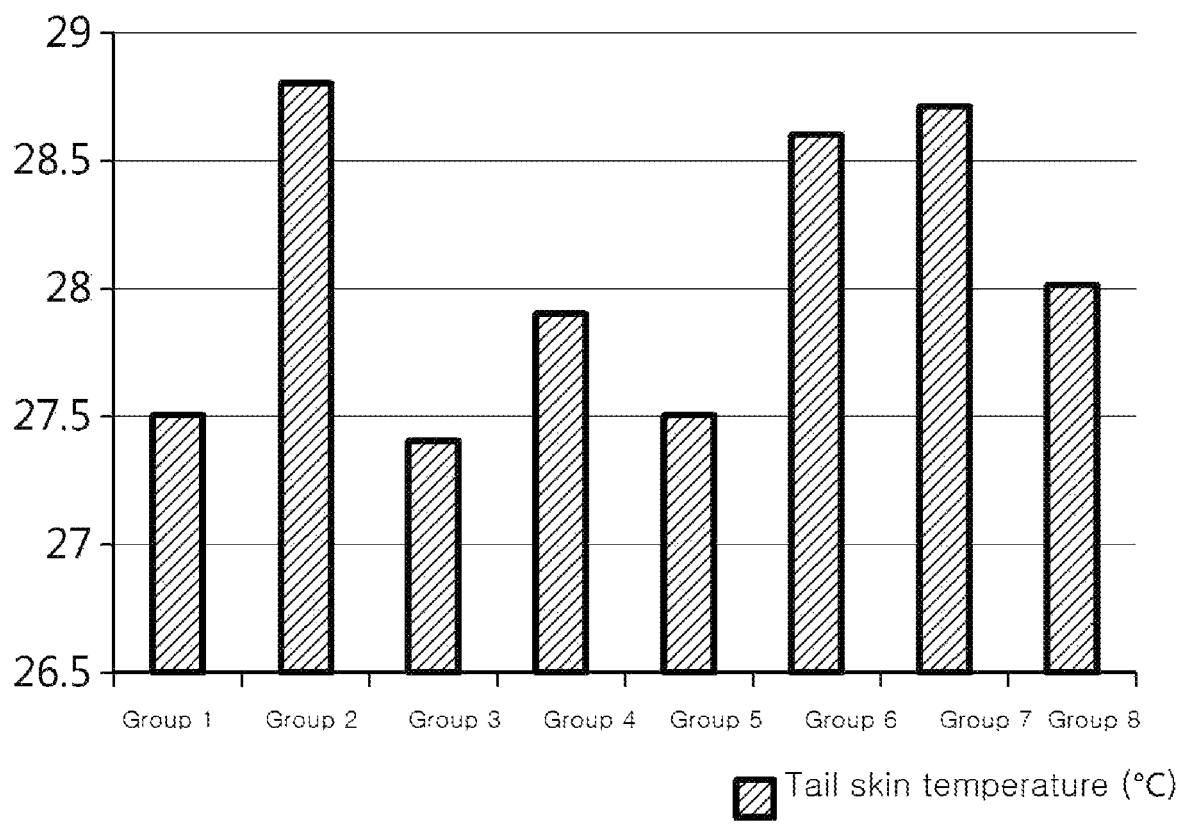
FIG. 1 is a graph showing the effect of remedying a vasomotor symptom of a mixture of three compounds tectorigenin 7-O-xylosylglucoside, tectorigenin, tectoridin according to an exemplary embodiment of the present disclosure.

Hereinafter, the present disclosure is described in detail through examples and test examples. However, the examples and test examples according to the present disclosure may be changed into various other forms, and it should not be construed that the scope of the present disclosure is limited to the examples and test examples. The examples and test examples of the present disclosure are provided to describe the present disclosure more completely to those of ordinary skill in the art.

[Sample Preparation]

Tectorigenin 7-O-xylosylglucoside was purchased from Tokiwa, and tectorigenin and tectoridin were purchased from Sigma-Aldrich.

Example 1. Evaluation of Activity for Estrogen Receptors of Tectorigenin 7-O-Xylosylglucoside, Tectorigenin, Tectoridin ERE (estrogen response element) reporter assay was performed to investigate the activity of the three compounds tectorigenin 7-O-xylosylglucoside, tectorigenin and tectoridin for estrogen receptors. Tectorigenin, tectoridin and tectorigenin 7-O-xylosylglucoside were treated at ratios described in Table 1 (the sum of the concentrations of the three compounds was 10 ppm). The experimental result with respect to a negative control group (1.0) is shown in Table 1.

TABLE 1

| | Ratio | | | Activity for estrogen receptors Fold induction |
|---|---|---|---|---|
| | Tectorigenin | Tectoridin | Tectorigenin 7-O-xylosylglucoside | |
| 1 | 0 | 0 | 1 | 34 |
| 2 | 1 | 1 | 1 | 66 |
| 3 | 1 | 0.5 | 0.5 | 54 |
| 4 | 1 | 0.5 | 5 | 46 |
| 5 | 1 | 0.5 | 20 | 37 |
| 6 | 1 | 5 | 0.5 | 68 |
| 7 | 1 | 5 | 5 | 75 |
| 8 | 1 | 5 | 20 | 42 |
| 9 | 1 | 20 | 0.5 | 66 |
| 10 | 1 | 20 | 5 | 60 |
| 11 | 1 | 20 | 20 | 51 |

As seen from Table 1, it was confirmed that the activity for estrogen receptors was excellent when the three compounds tectorigenin 7-O-xylosylglucoside, tectorigenin and tectoridin were treated together. In particular, it was found out that the activity varied depending on the ratio of the three compounds tectorigenin 7-O-xylosylglucoside, tectorigenin and tectoridin.

It was also confirmed that the activity for estrogen receptors was significantly low when the weight ratio of tectorigenin, tectoridin and tectorigenin 7-O-xylosylglucoside was outside the range of 1:0.5-20:0.5-20.

Example 2. Effect of Remedying Vasomotor Symptoms

It is known that 75% of postmenstrual women experience vasomotor symptoms. Facial flushing (hot flush) is the representative symptom where the skin on face, neck and chest is reddened abruptly, accompanied by unpleasant flushing and sweating. The change in the vasomotor symptoms can be evaluated by measuring the change in skin temperature. In an animal experiment, it can be measure by the skin temperature of the rat tail (Guidelines for evaluation of health functional food, 'Helpful for health of postmenstrual women', National Institute of Food and Drug Safety Evaluation).

11-12 week-old female Sprague-Dawley rats were subjected to sham operation (group 1, n=10) or ovariectomy (OVX) (groups 2-8, n=10 per each group). After a week from the operation, 0.01 mL of a sample per body weight (g) of each rat was administered orally every day for 4 weeks. 17β-Estradiol (E2) was administered to the positive control group and a 1:5:5 mixture of the three compounds tectorigenin, tectoridin and tectorigenin 7-O-xylosylglucoside was administered to the test groups. 4 weeks after the administration, the skin temperature at 2 cm where the tail starts was measured using an infrared thermometer. The measurement result is shown in FIG. 1.

TABLE 2

| Group | Operation | Sample |
|---|---|---|
| Group 1 | Sham | Drinking water |
| Group 2 | OVX | Drinking water |
| Group 3 | OVX | 17β-estradiol (E2), 0.5 mg/kg/day |
| Group 4 | OVX | T3*, 5 mg/kg/day |
| Group 5 | OVX | T3*, 10 mg/kg/day |
| Group 6 | OVX | Tectorigenin, 10 mg/kg/day |
| Group 7 | OVX | Tectoridin, 10 mg/kg/day |
| Group 8 | OVX | Tectorigenin 7-O-xylosylglucoside, 10 mg/kg/day |

*T3: 1:5:5 mixture of tectorigenin, tectoridin and tectorigenin 7-O-xylosylglucoside As seen from Table 3 and FIG. 1, it was confirmed that the administration of the mixture of the three compounds tectorigenin 7-O-xylosylglucoside, tectorigenin and tectoridin suppressed increase in the tail temperature caused by estrogen deficiency.

TABLE 3

| | Group | | | | | | | |
|---|---|---|---|---|---|---|---|---|
| | Group 1 | Group 2 | Group 3 | Group 4 | Group 5 | Group 6 | Group 7 | Group 8 |
| Tail skin temperature (□) | 27.5 | 28.8 | 27.4 | 27.9 | 27.5 | 28.6 | 28.7 | 28.0 |

Specifically, as can be seen from Table 3, among the three compounds tectorigenin 7-O-xylosylglucoside, tectorigenin and tectoridin, tectorigenin 7-O-xylosylglucoside showed the best effect of suppressing increase in the tail temperature as compared to tectorigenin and tectoridin. Meanwhile, group 4 and group 5 to which the three compounds tectorigenin 7-O-xylosylglucoside, tectorigenin and tectoridin were administered together showed the most suppressed increase in the tail skin temperature.

Example 3. Effect of Remedying Bone Resorption

In order to measure CTX (C-terminal telopeptide of type I collagen), which is a marker related with bone resorption, the same rats as in Example 2 were orally administered with a sample for 8 weeks and then serum was collected. The CTX level in the serum was measured using the rat C-telopeptide of type I collagen ELISA kit (MyBioSource) according to the manufacturer's instructions. The result is shown in FIG. 2.

As seen from FIG. 2 and Table 4, the group to which the three compounds tectorigenin 7-O-xylosylglucoside, tectorigenin and tectoridin mixture were administered showed significantly decreased CTX level as compared to the OVX group, suggesting that bone resorption was decreased.

TABLE 4

| | Group | | | | | | | |
|---|---|---|---|---|---|---|---|---|
| | Group 1 | Group 2 | Group 3 | Group 4 | Group 5 | Group 6 | Group 7 | Group 8 |
| CTX (ng/ml) | 42.3 | 78.2 | 52.6 | 60.7 | 49.1 | 71.5 | 70.4 | 58.4 |

Specifically, as can be seen from Table 4, among the three compounds tectorigenin 7-O-xylosylglucoside, tectorigenin and tectoridin, tectorigenin 7-O-xylosylglucoside showed the most inhibited bone resorption as compared to tectorigenin and tectoridin. Meanwhile, group 5 to which the three compounds tectorigenin 7-O-xylosylglucoside, tectorigenin and tectoridin were administered together showed the most inhibited bone resorption.

INDUSTRIAL APPLICABILITY

Because a composition according to the present disclosure shows quick effects for preventing, remedying and/or treating sweating, facial flushing and/or osteoporosis, it can be utilized for the hormone replacement therapy (HRT) used for preventing or remedying climacteric syndrome symptoms.

In addition, because the composition according to the present disclosure has no cytotoxicity unlike existing therapeutic agents for sweating, facial flushing or osteoporosis, and is safe with few side effects as much as it can be used as food, it can be utilized as a therapeutic agent for sweating, facial flushing or osteoporosis occurring in climacteric women.

The composition of the present disclosure can extend the time of suppressing facial flushing and sweating and is also effective in decreasing bone resorption.

The composition of the present disclosure may be used as a pharmaceutical composition, a food composition, a cosmetic composition, etc.

What is claimed is:

1. A method for treating, or remedying female climacteric syndrome symptoms by administering an effective amount of tectorigenin 7-O-xylosylglucoside to a subject in need thereof.

2. The method according to claim 1, wherein tectorigenin, tectoridin or a mixture thereof is further administered to the subject.

3. The method according to claim 1, wherein the female climacteric syndrome symptom is one or more selected from a group consisting of facial flushing, sweating and osteoporosis.

4. The method according to claim 2, wherein the method comprises administering daily dose of 10-500 mg of tectorigenin, tectoridin and tectorigenin 7-O-xylosylglucoside to the subject.

5. The method according to claim 2, wherein the method comprises administering tectorigenin, tectoridin and tectorigenin 7-O-xylosylglucoside at a weight ratio of 1:0.5-20:0.5-20 (tectorigenin:tectoridin:tectorigenin 7-O-xylosylglucoside) to the subject.

6. A method for treating, or remedying facial flushing symptoms by administering an effective amount of tectorigenin 7-O-xylosylglucoside to a subject in need thereof.

7. The method according to claim 6, wherein tectorigenin, tectoridin or a mixture thereof is further administered to the subject.

8. The method according to claim 7, wherein the method comprises administering daily dose of 10-500 mg of tectorigenin, tectoridin and tectorigenin 7-O-xylosylglucoside to the subject.

9. The method according to claim 7, wherein the method comprises administering tectorigenin, tectoridin and tectorigenin 7-O-xylosylglucoside at a weight ratio of 1:0.5-20:0.5-20 (tectorigenin:tectoridin:tectorigenin 7-O-xylosylglucoside) to the subject.

10. A method for treating, or remedying osteoporosis by administering an effective amount of tectorigenin 7-O-xylosylglucoside to a subject in need thereof.

11. The method according to claim 10, wherein tectorigenin, tectoridin or a mixture thereof is further administered to the subject.

12. The method according to claim 11, wherein the method comprises administering daily dose of 10-500 mg of tectorigenin, tectoridin and tectorigenin 7-O-xylosylglucoside to the subject.

13. The method according to claim 11, wherein the method comprises administering tectorigenin, tectoridin and tectorigenin 7-O-xylosylglucoside at a weight ratio of 1:0.5-20:0.5-20 (tectorigenin:tectoridin:tectorigenin 7-O-xylosylglucoside) to the subject.

14. A method for treating, or remedying sweating by administering an effective amount of tectorigenin 7-O-xylosylglucoside to a subject in need thereof.

15. The method according to claim 14, wherein tectorigenin, tectoridin or a mixture thereof is further administered to the subject.

16. The method according to claim 15, wherein the method comprises administering daily dose of 10-500 mg of tectorigenin, tectoridin and tectorigenin 7-O-xylosylglucoside to the subject.

17. The method according to claim 15, wherein the method comprises administering tectorigenin, tectoridin and tectorigenin 7-O-xylosylglucoside at a weight ratio of 1:0.5-20:0.5-20 (tectorigenin:tectoridin:tectorigenin 7-O-xylosylglucoside) to the subject.

* * * * *